(12) United States Patent
Yoshimoto et al.

(10) Patent No.: US 10,975,370 B2
(45) Date of Patent: Apr. 13, 2021

(54) METHODS FOR SCREENING NUCLEIC ACID APTAMERS

(71) Applicants: THE UNIVERSITY OF TOKYO, Tokyo (JP); NISSAN CHEMICAL CORPORATION, Tokyo (JP)

(72) Inventors: Keitaro Yoshimoto, Tokyo (JP); Koji Wakui, Tokyo (JP); Hitoshi Furusho, Funabashi (JP)

(73) Assignees: THE UNIVERSITY OF TOKYO, Tokyo (JP); LINKBIO CO., LTD., Toride (JP)

( * ) Notice: Subject to any disclaimer, the term of this patent is extended or adjusted under 35 U.S.C. 154(b) by 344 days.

(21) Appl. No.: 16/071,836

(22) PCT Filed: Jan. 20, 2017

(86) PCT No.: PCT/JP2017/001873
§ 371 (c)(1),
(2) Date: Jul. 20, 2018

(87) PCT Pub. No.: WO2017/126646
PCT Pub. Date: Jul. 27, 2017

(65) Prior Publication Data
US 2020/0332281 A1    Oct. 22, 2020

(30) Foreign Application Priority Data
Jan. 22, 2016 (JP) .............................. JP2016-010415

(51) Int. Cl.
*C12N 15/10* (2006.01)
*C12N 15/115* (2010.01)
*C12Q 1/6811* (2018.01)

(52) U.S. Cl.
CPC ........ *C12N 15/1048* (2013.01); *C12N 15/115* (2013.01); *C12Q 1/6811* (2013.01); *C12N 2310/16* (2013.01); *C12Q 2525/205* (2013.01); *C12Q 2531/113* (2013.01); *C12Q 2541/101* (2013.01); *C12Q 2565/518* (2013.01)

(58) Field of Classification Search
None
See application file for complete search history.

(56) References Cited

FOREIGN PATENT DOCUMENTS

JP    2016-171795 A    9/2016

OTHER PUBLICATIONS

Rezenom et al., Separation and detection of individual submicron partivcles by capillary electrophoresis with laser-light-scattering detection, Analyst, vol. 132, pp. 1215-1222 (Year: 2007).*
International Search Report for PCT/JP2017/001873 dated Apr. 18, 2017.

(Continued)

*Primary Examiner* — Teresa E Strzelecka
(74) *Attorney, Agent, or Firm* — Birch, Stewart, Kolasch & Birch, LLP

(57) ABSTRACT

The present invention relates to a method for screening a nucleic acid aptamer comprising: (a) contacting a target molecule immobilized on a solid phase support with a nucleic acid aptamer candidate; (b) collecting the nucleic acid aptamer candidate binding with the target molecule by a capillary electrophoresis; and (c) amplifying the nucleic acid aptamer candidate by PCR.

7 Claims, 5 Drawing Sheets

Specification includes a Sequence Listing.

(56) References Cited

OTHER PUBLICATIONS

Mosing et al., "Capillary Electrophoresis-SELEX Selection of aptamers with affinity for HIV-1 reverse transcriptase", Analytical Chemistry, Oct. 1, 2005, vol. 77, No. 19, pp. 6107-6112.
Wakui et al., "Development of in vitro selection method for DNA aptamers based on the combined use of CE-SELEX and magnetic beads", Abstracts of the 96th CSJ Annual Meeting, Mar. 24, 2016, 1 PB-055, total 1 page.
Wakui et al., "In vitro selection of DNA aptamer by beads based capillary electrophoresis", Abstracts of the 43rd ISNAC, Sep. 27, 2016, pp. 252-253, total 4 pages.
Written Opinion of the International Searching Authority for PCT/JP2017/001873 (PCT/ISA/237) dated Apr. 18, 2017.
Yang et al., "Capillary electrophoresis-SELEX selection of catalytic DNA aptamers for a small-molecule porphyrin target", Analytical Chemistry, 2013, vol. 85, pp. 1525-1530.
Darmostuk et al., "Current approaches in SELEX: An update to aptamer selection technology," Biotechnology Advances (2015), vol. 33, pp. 1141-1161.
Extended European Search Report dated Aug. 13, 2019, in European Patent Application No. 17741523.9.
Lauridsen et al., "Rapid One-Step Selection Method for Generating Nucleic Acid Aptamers: Development of a DNA Aptamer against α-Bungarotoxin," PLos One (Jul. 2012), vol. 7, No. 7, e41702, pp. 1-6.
Song et al., "Aptamers and Their Biological Applications," Sensors (2012), vol. 12, pp. 612-631.
Wakui et al., "Rapidly Neutralizable and Highly Anticoagulant Thrombin-Binding DNA Aptamer Discovered by MACE SELEX," Molecular Therapy: Nucleic Acids (Jun. 2019), vol. 16, pp. 348-359.

\* cited by examiner

A

B

SEQUENCE LISTING

<160> NUMBER OF SEQ ID NOS: 64

<210> SEQ ID NO 1
<211> LENGTH: 70
<212> TYPE: DNA
<213> ORGANISM: Artificial Sequence
<220> FEATURE:
<223> OTHER INFORMATION: DNA Library

<400> SEQUENCE: 1
agcagcacag aggtcagatg gtttgggtgg ttaggtgttg acctgggatg cctatgcgtg    60
ctaccgtgaa                                                          70

<210> SEQ ID NO 2
<211> LENGTH: 70
<212> TYPE: DNA
<213> ORGANISM: Artificial Sequence
<220> FEATURE:
<223> OTHER INFORMATION: DNA Library

<400> SEQUENCE: 2
agcagcacag aggtcagatg gagtcgggtg gctattgggt atggaccgtg cctatgcgtg    60
ctaccgtgaa                                                          70

<210> SEQ ID NO 3
<211> LENGTH: 70
<212> TYPE: DNA
<213> ORGANISM: Artificial Sequence
<220> FEATURE:
<223> OTHER INFORMATION: DNA Library

<400> SEQUENCE: 3
agcagcacag aggtcagatg gatggtgtag gttgggagag gctcagtgcc cctatgcgtg    60
ctaccgtgaa                                                          70

<210> SEQ ID NO 4
<211> LENGTH: 70
<212> TYPE: DNA
<213> ORGANISM: Artificial Sequence
<220> FEATURE:
<223> OTHER INFORMATION: DNA Library

<400> SEQUENCE: 4
agcagcacag aggtcagatg ttggtggggt ggctttgggt atttacttgg cctatgcgtg    60
ctaccgtgaa                                                          70

<210> SEQ ID NO 5
<211> LENGTH: 70
<212> TYPE: DNA
<213> ORGANISM: Artificial Sequence
<220> FEATURE:
<223> OTHER INFORMATION: DNA Library

<400> SEQUENCE: 5
agcagcacag aggtcagatg gtggatttgg gtggattggt atgaactgac cctatgcgtg    60
ctaccgtgaa                                                          70

<210> SEQ ID NO 6
<211> LENGTH: 70
<212> TYPE: DNA
<213> ORGANISM: Artificial Sequence
<220> FEATURE:
<223> OTHER INFORMATION: DNA Library

<400> SEQUENCE: 6
agcagcacag aggtcagatg gttgggtagg gttggatagg ggcaagtaga cctatgcgtg    60
ctaccgtgaa                                                          70

<210> SEQ ID NO 7

-continued

```
<211> LENGTH: 70
<212> TYPE: DNA
<213> ORGANISM: Artificial Sequence
<220> FEATURE:
<223> OTHER INFORMATION: DNA Library

<400> SEQUENCE: 7
agcagcacag aggtcagatg gtgtactatt atggtgtggt tggtatggtt cctatgcgtg    60
ctaccgtgaa                                                           70

<210> SEQ ID NO 8
<211> LENGTH: 70
<212> TYPE: DNA
<213> ORGANISM: Artificial Sequence
<220> FEATURE:
<223> OTHER INFORMATION: DNA Library

<400> SEQUENCE: 8
agcagcacag aggtcagatg ggttgggtgg tgtgggtagt gatccctgtg cctatgcgtg    60
ctaccgtgaa                                                           70

<210> SEQ ID NO 9
<211> LENGTH: 70
<212> TYPE: DNA
<213> ORGANISM: Artificial Sequence
<220> FEATURE:
<223> OTHER INFORMATION: DNA Library

<400> SEQUENCE: 9
agcagcacag aggtcagatg tggattggtt ggattgggggg tgtgactgtg cctatgcgtg   60
ctaccgtgaa                                                           70

<210> SEQ ID NO 10
<211> LENGTH: 70
<212> TYPE: DNA
<213> ORGANISM: Artificial Sequence
<220> FEATURE:
<223> OTHER INFORMATION: DNA Library

<400> SEQUENCE: 10
agcagcacag aggtcagatg tcgggttgga ttggttggct taaactatgt cctatgcgtg    60
ctaccgtgaa                                                           70

<210> SEQ ID NO 11
<211> LENGTH: 71
<212> TYPE: DNA
<213> ORGANISM: Artificial Sequence
<220> FEATURE:
<223> OTHER INFORMATION: DNA Library

<400> SEQUENCE: 11
agcagcacag aggtcagatg tctggttggt gtggttggga gtttttttgat ccctatgcgt   60 gctaccgtga a                                                         71

<210> SEQ ID NO 12
<211> LENGTH: 70
<212> TYPE: DNA
<213> ORGANISM: Artificial Sequence
<220> FEATURE:
<223> OTHER INFORMATION: DNA Library

<400> SEQUENCE: 12
agcagcacag aggtcagatg gatggtgtag gttgggagag gctcagtgcc cctatgcgtg    60
```

```
ctaccgtgaa                                                            70

<210> SEQ ID NO 13
<211> LENGTH: 70
<212> TYPE: DNA
<213> ORGANISM: Artificial Sequence
<220> FEATURE:
<223> OTHER INFORMATION: DNA Library

<400> SEQUENCE: 13
agcagcacag aggtcagatg gtttgggtgg ttaggtgttg acctgggatg cctatgcgtg     60
ctaccgtgaa                                                            70

<210> SEQ ID NO 14
<211> LENGTH: 69
<212> TYPE: DNA
<213> ORGANISM: Artificial Sequence
<220> FEATURE:
<223> OTHER INFORMATION: DNA Library

<400> SEQUENCE: 14
agcagcacag aggtcagatg gatggtgtag gttgggagag gctcagtgcc ctatgcgtgc     60
taccgtgaa                                                             69

<210> SEQ ID NO 15
<211> LENGTH: 70
<212> TYPE: DNA
<213> ORGANISM: Artificial Sequence
<220> FEATURE:
<223> OTHER INFORMATION: DNA Library

<400> SEQUENCE: 15
agcagcacag aggtcagatg ttagggttgg gagggtggct gactaatgta cctatgcgtg     60
ctaccgtgaa                                                            70

<210> SEQ ID NO 16
<211> LENGTH: 70
<212> TYPE: DNA
<213> ORGANISM: Artificial Sequence
<220> FEATURE:
<223> OTHER INFORMATION: DNA Library

<400> SEQUENCE: 16
agcagcacag aggtcagatg gagtcgggtg gctattgggt atggaccgtg cctatgcgtg     60
ctaccgtgaa                                                            70

<210> SEQ ID NO 17
<211> LENGTH: 70
<212> TYPE: DNA
<213> ORGANISM: Artificial Sequence
<220> FEATURE:
<223> OTHER INFORMATION: DNA Library

<400> SEQUENCE: 17
agcagcacag aggtcagatg gggttggatt gggtggcggt gtgaactatg cctatgcgtg     60
ctaccgtgaa                                                            70

<210> SEQ ID NO 18
<211> LENGTH: 70
<212> TYPE: DNA
<213> ORGANISM: Artificial Sequence
<220> FEATURE:
```

```
<223> OTHER INFORMATION: DNA Library

<400> SEQUENCE: 18
agcagcacag aggtcagatg gttggttatg gtggttttag tgggactcga cctatgcgtg      60
ctaccgtgaa                                                             70

<210> SEQ ID NO 19
<211> LENGTH: 69
<212> TYPE: DNA
<213> ORGANISM: Artificial Sequence
<220> FEATURE:
<223> OTHER INFORMATION: DNA Library

<400> SEQUENCE: 19
agcagcacag aggtcagatg ataggatggg tgggtgggtt cgtcagttac ctatgcgtgc      60
taccgtgaa                                                              69

<210> SEQ ID NO 20
<211> LENGTH: 70
<212> TYPE: DNA
<213> ORGANISM: Artificial Sequence
<220> FEATURE:
<223> OTHER INFORMATION: DNA Library

<400> SEQUENCE: 20
agcagcacag aggtcagatg tgggtccggg gttgggggggg tggccgggtc cctatgcgtg     60
ctaccgtgaa                                                             70

<210> SEQ ID NO 21
<211> LENGTH: 70
<212> TYPE: DNA
<213> ORGANISM: Artificial Sequence
<220> FEATURE:
<223> OTHER INFORMATION: DNA Library

<400> SEQUENCE: 21
agcagcacag aggtcagatg gggtggggtg gattggttgg cgttcctgga cctatgcgtg      60
ctaccgtgaa                                                             70

<210> SEQ ID NO 22
<211> LENGTH: 70
<212> TYPE: DNA
<213> ORGANISM: Artificial Sequence
<220> FEATURE:
<223> OTHER INFORMATION: DNA Library

<400> SEQUENCE: 22
agcagcacag aggtcagatg aagagggtgg agtggttggc ttcacaatgg cctatgcgtg      60
ctaccgtgaa                                                             70

<210> SEQ ID NO 23
<211> LENGTH: 70
<212> TYPE: DNA
<213> ORGANISM: Artificial Sequence
<220> FEATURE:
<223> OTHER INFORMATION: DNA Library

<400> SEQUENCE: 23
agcagcacag aggtcagatg gttggttatg gtggttttag tgggactcga cctatgcgtg      60
ctaccgtgaa                                                             70
```

```
<210> SEQ ID NO 24
<211> LENGTH: 70
<212> TYPE: DNA
<213> ORGANISM: Artificial Sequence
<220> FEATURE:
<223> OTHER INFORMATION: DNA Library

<400> SEQUENCE: 24
agcagcacag aggtcagatg ggggtggatg tggtattttta gtggcgatct cctatgcgtg      60
ctaccgtgaa                                                              70

<210> SEQ ID NO 25
<211> LENGTH: 70
<212> TYPE: DNA
<213> ORGANISM: Artificial Sequence
<220> FEATURE:
<223> OTHER INFORMATION: DNA Library

<400> SEQUENCE: 25
agcagcacag aggtcagatg aaggggtgg gggtcgggtg gcctcacgat cctatgcgtg        60
ctaccgtgaa                                                              70

<210> SEQ ID NO 26
<211> LENGTH: 70
<212> TYPE: DNA
<213> ORGANISM: Artificial Sequence
<220> FEATURE:
<223> OTHER INFORMATION: DNA Library

<400> SEQUENCE: 26
agcagcacag aggtcagatg ggatggattg gttggcgtct gataatggtg cctatgcgtg       60
ctaccgtgaa                                                              70

<210> SEQ ID NO 27
<211> LENGTH: 70
<212> TYPE: DNA
<213> ORGANISM: Artificial Sequence
<220> FEATURE:
<223> OTHER INFORMATION: DNA Library

<400> SEQUENCE: 27
agcagcacag aggtcagatg gtttgggtgg ttaggtgttg acctgggatg cctatgcgtg       60
ctaccgtgaa                                                              70

<210> SEQ ID NO 28
<211> LENGTH: 70
<212> TYPE: DNA
<213> ORGANISM: Artificial Sequence
<220> FEATURE:
<223> OTHER INFORMATION: DNA Library

<400> SEQUENCE: 28
agcagcacag aggtcagatg gatggtgtag gttgggagag gctcagtgcc cctatgcgtg       60
ctaccgtgaa                                                              70

<210> SEQ ID NO 29
<211> LENGTH: 70
<212> TYPE: DNA
<213> ORGANISM: Artificial Sequence
<220> FEATURE:
<223> OTHER INFORMATION: DNA Library

<400> SEQUENCE: 29
```
agcagcacag aggtcagatg ttggtggggt ggctttgggt atttacttgg cctatgcgtg    60
ctaccgtgaa    70

<210> SEQ ID NO 30
<211> LENGTH: 70
<212> TYPE: DNA
<213> ORGANISM: Artificial Sequence
<220> FEATURE:
<223> OTHER INFORMATION: DNA Library

<400> SEQUENCE: 30
agcagcacag aggtcagatg ggggatggtt agggtggctt aatattgacc cctatgcgtg    60
ctaccgtgaa    70

<210> SEQ ID NO 31
<211> LENGTH: 69
<212> TYPE: DNA
<213> ORGANISM: Artificial Sequence
<220> FEATURE:
<223> OTHER INFORMATION: DNA Library

<400> SEQUENCE: 31
agcagcacag aggtcagatg acggggatgg gggggtggag gaggcctgtc ctatgcgtgc    60
taccgtgaa    69

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
agcagcacag aggtcagatg    20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ttcacggtag cacgcatagg    20

<210> SEQ ID NO 34
<211> LENGTH: 30
<212> TYPE: DNA
<213> ORGANISM: Artificial Sequence
<220> FEATURE:
<223> OTHER INFORMATION: Aptamer

<400> SEQUENCE: 34
gtttgggtgg ttaggtgttg acctgggatg    30

<210> SEQ ID NO 35
<211> LENGTH: 30
<212> TYPE: DNA
<213> ORGANISM: Artificial Sequence
<220> FEATURE:
<223> OTHER INFORMATION: Aptamer

<400> SEQUENCE: 35
gagtcgggtg gctattgggt atggaccgtg    30

<210> SEQ ID NO 36
<211> LENGTH: 30
<212> TYPE: DNA
<213> ORGANISM: Artificial Sequence
<220> FEATURE:
<223> OTHER INFORMATION: Aptamer

<400> SEQUENCE: 36
gatggtgtag gttgggagag gctcagtgcc                                    30

<210> SEQ ID NO 37
<211> LENGTH: 30
<212> TYPE: DNA
<213> ORGANISM: Artificial Sequence
<220> FEATURE:
<223> OTHER INFORMATION: Aptamer

<400> SEQUENCE: 37
ttggtggggt ggctttgggt atttacttgg                                    30

<210> SEQ ID NO 38
<211> LENGTH: 30
<212> TYPE: DNA
<213> ORGANISM: Artificial Sequence
<220> FEATURE:
<223> OTHER INFORMATION: Aptamer

<400> SEQUENCE: 38
gtggatttgg gtggattggt atgaactgac                                    30

<210> SEQ ID NO 39
<211> LENGTH: 30
<212> TYPE: DNA
<213> ORGANISM: Artificial Sequence
<220> FEATURE:
<223> OTHER INFORMATION: Aptamer

<400> SEQUENCE: 39
gttgggtagg gttggatagg ggcaagtaga                                    30

<210> SEQ ID NO 40
<211> LENGTH: 30
<212> TYPE: DNA
<213> ORGANISM: Artificial Sequence
<220> FEATURE:
<223> OTHER INFORMATION: Aptamer

<400> SEQUENCE: 40
gtgtactatt atggtgtggt tggtatggtt                                    30

<210> SEQ ID NO 41
<211> LENGTH: 30
<212> TYPE: DNA
<213> ORGANISM: Artificial Sequence
<220> FEATURE:
<223> OTHER INFORMATION: Aptamer

<400> SEQUENCE: 41
ggttgggtgg tgtgggtagt gatccctgtg                                    30

<210> SEQ ID NO 42
<211> LENGTH: 30
<212> TYPE: DNA
<213> ORGANISM: Artificial Sequence
<220> FEATURE:

<223> OTHER INFORMATION: Aptamer

<400> SEQUENCE: 42
tggattggtt ggattggggg tgtgactgtg                                        30

<210> SEQ ID NO 43
<211> LENGTH: 30
<212> TYPE: DNA
<213> ORGANISM: Artificial Sequence
<220> FEATURE:
<223> OTHER INFORMATION: Aptamer

<400> SEQUENCE: 43
tcgggttgga ttggttggct taaactatgt                                        30

<210> SEQ ID NO 44
<211> LENGTH: 31
<212> TYPE: DNA
<213> ORGANISM: Artificial Sequence
<220> FEATURE:
<223> OTHER INFORMATION: Aptamer

<400> SEQUENCE: 44
tctggttggt gtggttggga gtttttttgat c                                     31

<210> SEQ ID NO 45
<211> LENGTH: 30
<212> TYPE: DNA
<213> ORGANISM: Artificial Sequence
<220> FEATURE:
<223> OTHER INFORMATION: Aptamer

<400> SEQUENCE: 45
gatggtgtag gttgggagag gctcagtgcc                                        30

<210> SEQ ID NO 46
<211> LENGTH: 30
<212> TYPE: DNA
<213> ORGANISM: Artificial Sequence
<220> FEATURE:
<223> OTHER INFORMATION: Aptamer

<400> SEQUENCE: 46
gtttgggtgg ttaggtgttg acctgggatg                                        30

<210> SEQ ID NO 47
<211> LENGTH: 29
<212> TYPE: DNA
<213> ORGANISM: Artificial Sequence
<220> FEATURE:
<223> OTHER INFORMATION: Aptamer

<400> SEQUENCE: 47
gatggtgtag gttgggagag gctcagtgc                                         29

<210> SEQ ID NO 48
<211> LENGTH: 30
<212> TYPE: DNA
<213> ORGANISM: Artificial Sequence
<220> FEATURE:
<223> OTHER INFORMATION: Aptamer

<400> SEQUENCE: 48
ttagggttgg gagggtggct gactaatgta                                        30

```
<210> SEQ ID NO 49
<211> LENGTH: 30
<212> TYPE: DNA
<213> ORGANISM: Artificial Sequence
<220> FEATURE:
<223> OTHER INFORMATION: Aptamer

<400> SEQUENCE: 49
gagtcgggtg gctattgggt atggaccgtg                                        30

<210> SEQ ID NO 50
<211> LENGTH: 30
<212> TYPE: DNA
<213> ORGANISM: Artificial Sequence
<220> FEATURE:
<223> OTHER INFORMATION: Aptamer

<400> SEQUENCE: 50
gggttggatt gggtggcggt gtgaactatg                                        30

<210> SEQ ID NO 51
<211> LENGTH: 30
<212> TYPE: DNA
<213> ORGANISM: Artificial Sequence
<220> FEATURE:
<223> OTHER INFORMATION: Aptamer

<400> SEQUENCE: 51
gttggttatg gtggttttag tgggactcga                                        30

<210> SEQ ID NO 52
<211> LENGTH: 29
<212> TYPE: DNA
<213> ORGANISM: Artificial Sequence
<220> FEATURE:
<223> OTHER INFORMATION: Aptamer

<400> SEQUENCE: 52
ataggatggg tgggtgggtt cgtcagtta                                         29

<210> SEQ ID NO 53
<211> LENGTH: 30
<212> TYPE: DNA
<213> ORGANISM: Artificial Sequence
<220> FEATURE:
<223> OTHER INFORMATION: Aptamer

<400> SEQUENCE: 53
tgggtccggg gttgggggggg tggccgggtc                                       30

<210> SEQ ID NO 54
<211> LENGTH: 30
<212> TYPE: DNA
<213> ORGANISM: Artificial Sequence
<220> FEATURE:
<223> OTHER INFORMATION: Aptamer

<400> SEQUENCE: 54
gggtggggtg gattggttgg cgttcctgga                                        30

<210> SEQ ID NO 55
<211> LENGTH: 30
<212> TYPE: DNA
<213> ORGANISM: Artificial Sequence
<220> FEATURE:
<223> OTHER INFORMATION: Aptamer
```

```
<400> SEQUENCE: 55
aagagggtgg agtggttggc ttcacaatgg                                           30

<210> SEQ ID NO 56
<211> LENGTH: 30
<212> TYPE: DNA
<213> ORGANISM: Artificial Sequence
<220> FEATURE:
<223> OTHER INFORMATION: Aptamer

<400> SEQUENCE: 56
gttggttatg gtggttttag tgggactcga                                           30

<210> SEQ ID NO 57
<211> LENGTH: 30
<212> TYPE: DNA
<213> ORGANISM: Artificial Sequence
<220> FEATURE:
<223> OTHER INFORMATION: Aptamer

<400> SEQUENCE: 57
ggggtggatg tggtatttta gtggcgatct                                           30

<210> SEQ ID NO 58
<211> LENGTH: 30
<212> TYPE: DNA
<213> ORGANISM: Artificial Sequence
<220> FEATURE:
<223> OTHER INFORMATION: Aptamer

<400> SEQUENCE: 58 aaggggtgg gggtcgggtg gcctcacgat                                            30

<210> SEQ ID NO 59
<211> LENGTH: 30
<212> TYPE: DNA
<213> ORGANISM: Artificial Sequence
<220> FEATURE:
<223> OTHER INFORMATION: Aptamer

<400> SEQUENCE: 59
ggatggattg gttggcgtct gataatggtg                                           30

<210> SEQ ID NO 60
<211> LENGTH: 30
<212> TYPE: DNA
<213> ORGANISM: Artificial Sequence
<220> FEATURE:
<223> OTHER INFORMATION: Aptamer

<400> SEQUENCE: 60
gtttgggtgg ttaggtgttg acctgggatg                                           30

<210> SEQ ID NO 61
<211> LENGTH: 30
<212> TYPE: DNA
<213> ORGANISM: Artificial Sequence
<220> FEATURE:
<223> OTHER INFORMATION: Aptamer

<400> SEQUENCE: 61
gatggtgtag gttgggagag gctcagtgcc                                           30

<210> SEQ ID NO 62
<211> LENGTH: 30
```

```
<212> TYPE: DNA
<213> ORGANISM: Artificial Sequence
<220> FEATURE:
<223> OTHER INFORMATION: Aptamer

<400> SEQUENCE: 62
ttggtggggt ggctttgggt atttacttgg                                        30

<210> SEQ ID NO 63
<211> LENGTH: 30
<212> TYPE: DNA
<213> ORGANISM: Artificial Sequence
<220> FEATURE:
<223> OTHER INFORMATION: Aptamer

<400> SEQUENCE: 63
ggggatggtt agggtggctt aatattgacc                                        30

<210> SEQ ID NO 64
<211> LENGTH: 29
<212> TYPE: DNA
<213> ORGANISM: Artificial Sequence
<220> FEATURE:
<223> OTHER INFORMATION: Aptamer

<400> SEQUENCE: 64
acggggatgg gggggtggag gaggcctgt                                         29
```

METHODS FOR SCREENING NUCLEIC ACID APTAMERS

REFERENCE TO SEQUENCE LISTING SUBMITTED VIA EFS-WEB

This application includes an electronically submitted sequence listing in .txt format. The .txt file contains a sequence listing entitled "0283_0443PUS1_ST25.txt" created on Oct. 26, 2020 and is 14,482 bytes in size. The sequence listing contained in this .txt file is part of the specification and is hereby incorporated by reference herein in its entirety.

TECHNICAL FIELD

The present invention is related to methods for screening nucleic acid aptamers.

BACKGROUND ART

A nucleic acids aptamer is a single-stranded DNA or RNA with a molecular recognition ability and it has been reported in 1990 for the first time by Ellington and others and Tuerk and others. Nucleic acid aptamers may be obtained by evolutionary engineering methods such as Systematic Evolution of Ligands by Exponential enrichment (SELEX), and there are a large number of reports on nucleic acid aptamers having a binding ability and specificity comparable to those of an antibody. Moreover, in addition to proteins and cells, aptamers against various targets such as low molecular compounds whose antibodies are difficult to be obtained are obtainable, and the application of nucleic acid aptamers on therapeutic drugs and diagnostic drugs are awaited. Nonetheless, whereas the yield rate of an antibody is 90% or more, the yield rate of current nucleic acid aptamers is said to be 30% or less. In other words, the improvement of techniques on the nucleic acid aptamer yield rate is a key issue for nucleic acids aptamers to be widely and industrially used from now onwards.

Nucleic acid aptamers have drawn attention as a novel molecular recognition element that could replace antibodies; however, the yield rate of nucleic acid aptamer is 30% or less, and the development of a highly efficient method for obtaining aptamers is desired. CE-SELEX is a rapid nucleic acid aptamer screening method utilizing the superior separation ability of capillary electrophoresis. However, poor versatility of this method has to be admitted due to the difficulty in designing experimental conditions (designing the collection region) and to the restriction it has in that the target molecule has to be of a certain size so that the electrophoretic mobility greatly varies when the target molecule binds with an ssDNA library.

In CE-SELEX, designing the collection region is an important key factor which determines the aptamer yield rate. Moreover, it is necessary to collect a region which would certainly include an ssDNA library forming a complex with the target without contamination of an ssDNA library which does not have the binding ability to the target. An ideal collection region is of a peak range deriving from the complex of the ssDNA library and the target. Nonetheless, the target molecule easily interacts with ssDNA such as a MutS protein, and it is difficult to detect a complex of an ssDNA library and a target without using a highly-sensitive fluorescence detector. Until now, various inputs were made for the optimization of the collection region such as visualization of the target proteins by fluorescent modification and prediction of the detection site of target/aptamer complex using a real-time PCR. Nonetheless, despite of that, detecting the complex has been a difficult task, and thus, designing the collection region to be from the detection site of the target molecule to immediately before the detection of the ssDNA library has been commonly carried out. Such design method of the collection region has a problem in that a sequence with low binding ability which has dissociated in the meantime may likely be included in the collection region (FIG. 1A).

When a small molecular such as a low molecular compound is targeted, the change in electrophoretic mobility caused by the binding with the ssDNA library is almost null, and thus, the application of CE-SELEX is considered to be difficult. Until today, only one report has been made regarding obtaining an aptamer against a low molecular compound by using CE-SELEX, which demonstrates the difficulty of this issue (Non-Patent Document 1).

PRIOR ART DOCUMENTS

Non-Patent Documents

Non-Patent Document 1: Yang, J. & Bowser, M. T. Capillary Electrophoresis-SELEX Selection of Catalytic DNA Aptamers for a Small-Molecule Porphyrin Target. Anal. Chem. 85, 1525-1530 (2013).

SUMMARY OF INVENTION

Technical Problem

The present invention provides a novel CE-SELEX which remains with the advantages of CE-SELEX but which overcame the drawbacks such as difficulty in designing experimental conditions and limitation in the kinds of target molecules that are applicable. More specifically, the present invention relates to a method for screening a nucleic acid aptamer using the combination of particles and CE-SELEX. To date, quantitative analysis methods of RNA and antigens using the combination of particles and capillary electrophoresis have been reported; however, methods combining particles and CE-SELEX have not yet been reported.

Solution to Problem

As a result of dedicated research, the present inventors found that the conventional problem could be solved by combining particles and CE-SELEX, and thus, completed the present invention. The present invention is as follows:

[1] A method for screening a nucleic acid aptamer comprising:
(a) contacting a target molecule immobilized on a solid phase support with a nucleic acid aptamer candidate;
(b) collecting the nucleic acid aptamer candidate binding with the target molecule by a capillary electrophoresis;
(c) amplifying the nucleic acid aptamer candidate by PCR;
[2] the method according to [1] further comprising (d) making the amplified PCR product into a single strand;
[3] the method according to [1] or [2], wherein the solid phase support is a particle;
[4] the method according to any one of [1] to [3], wherein the minimum value of the particle size of the particle is 0.05 µm;
[5] the method according to any one of [1] to [4], wherein the target molecule is a protein or a low molecular compound;

[6] the method according to any one of [1] to [5], wherein the nucleic acid aptamer candidate is a single-stranded DNA library;

[7] the method according to any one of [2] to [6], wherein the steps (a) to (d) are repeated for a maximum of three times.

As for the solid phase support, any solid phase support that can immobilize a target molecule on the surface can be used. For example, laminated graphenes, carbon nanotubes, fullerenes, and particles may be included. As for the particles, any conventionally known particles may be used. For example, silica beads, polystyrene beads, latex beads, and metal colloids may be included. The particles of the present invention may be magnetic particles. The maximum value of the average particle size of the particles can be determined depending on the inner diameter of the capillary. Preferably, this is 100 µm, more preferably, 10 µm, and even more preferably, 1 µm. The minimum value of the average particle size of the particles is preferably, 100 nm, more preferably, 10 nm, and even more preferably, 1 nm. The average particle size of a particle could be determined by using any known methods. For example, sieving method, microscopy method, sedimentation method, laser diffraction scattering method, and electrical detection method may be included. Preferably, microscopy method is used.

For using an absorbance detector of a visible light portion without using an expensive fluorescence detector, the particles should have a sufficient particle size so that they would be detected by the scattering of visible light. In this case, the minimum value of the average particle size of the particle is preferably, 0.05 µm, more preferably, 0.5 µm, and even more preferably, 5 µm.

In the present invention, a target molecule refers to a molecule which serves as a target of detection in the detection method and the like utilizing a nucleic acid aptamer. The chemical species of the target molecules are not particularly limited, and may include various chemical species such as low-molecular compounds, macromolecules, and biological substances. Furthermore, target molecules may be immobilized on the surface of a solid phase support. More specifically, sugar, fats, oligopeptides, proteins, and nucleic acids may be included, for example. As the target molecules, for example, antigens, antibodies, ligands, receptors, interacting proteins, and the like, may be included.

In the present invention, a nucleic acid aptamer refers to a nucleic acid molecule which has a high binding affinity to a predetermined target molecule and thereby can specifically bind to the target molecule. Nucleic acid molecules having such properties are called as nucleic acid aptamers, and unless particularly noted otherwise, they are not restricted by the base sequence, molecular size, molecular conformational structure, and the like. Preferably, the nucleic acid aptamer is a single-stranded RNA or DNA.

In the present invention, a target molecule immobilized on a solid phase support refers to a target molecule being immobilized on a solid phase support surface by such as hydrophobic interaction, electrostatic interaction, covalent bond, coordination bond, and noncovalent intermolecular action (such as biotin-streptavidin).

In the present invention, a nucleic acid aptamer candidate refers to a pool constituted of a plural number of RNA and/or DNA. Preferably, it is of a single-stranded nucleic acid library consisting of a single-stranded nucleic acid, and more preferably, a single-stranded DNA library consisting of a single-stranded DNA. Furthermore, a double-stranded nucleic acid formed by part or all of the bases of the single-stranded nucleic acid forming a pair with each other may be included in part.

In the present invention, capillary electrophoresis refers to filling the capillary with aqueous solution, introducing an aqueous solution containing the target product, and by placing this under electric field, actions such as charge transfer, affinity, and electroosmotic flow take place, which allows the separation purification. In addition, any inner diameter of the capillary may be used.

In the present invention, a nucleic acid aptamer candidate bound with a target molecule is collected by a capillary electrophoresis. To a capillary electrophoresis system, a previously pre-treated capillary tube is disposed. Then, a sample in which an ssDNA library and particles immobilized with a target substance being mixed is injected, and electrophoresis is carried out in a running buffer. During electrophoresis, for example, absorbance in wave lengths such as 195, 260, 280, and 550 nm is measured over time by using a diode array detector, and with the obtained peak as an indicator, the recovery of the magnetic particle portions could be carried out (step (a) and step (b)).

In the present invention, a collected nucleic acid aptamer candidate is amplified by PCR. PCR is a polymerase chain reaction which allows a specific DNA region to be amplified to several hundreds of thousands of times by repeating a DNA synthesis reaction using a DNA synthetase in vitro. The primer used here varies depending on the immobilized sequence of the DNA library (the complementary sequence of the primer sequence) to be used; however, it may include AGCAGCACAGAGGTCAGATG (forward primer) (SEQ ID NO:32) and TTCACGGTAGCACGCATAGG (reverse primer) (SEQ ID NO:33), for example. DNA polymerase, Tris-HCl, KCl, $MgCl_2$, and dNTPs are mixed with the primers and the collected nucleic acid aptamer candidates, heating temperature and time were adjusted in a thermal cycler, and by repeating this cycle, a DNA region can be amplified (step (c)).

In the present invention, in some occasions, an amplified PCR product is made into a single strand. For example, the following step is adequately repeated: mixing streptavidin-immobilized magnetic particles (for example, magnosphere MS300/Streptavidin (Invitrogen) and the like) with an amplified PCR product using a biotinylated primer; removing the supernatant; and washing. Subsequently, NaOH of an appropriate concentration is added to allow the elution of the target ssDNA from the magnetic particle surface and this is recovered (step (d)).

In the present invention, the above-mentioned steps (a) to (d) may be optionally repeated. Preferably, the above-mentioned steps (a) to (d) are repeated for a maximum of three times.

Advantageous Effects of the Invention

The present invention is a very simple method which has only immobilized a target molecule onto a particle surface; however, this method could theoretically solve almost all of the problems CE-SELEX had until now. First of all, designing a collection region in CE-SELEX using magnetic particles of the present invention (hereinafter, referred to as MB-CE-SELEX) is far much easier as compared to that of the conventional CE-SELEX. Moreover, as the particles can be detected by an absorbance detector with high sensitivity using light scattering, it does not require an expensive fluorescence detector. Moreover, for any target molecule, the peak deriving from the magnetic particles can be set as the collection region (FIG. 2). In addition, by precisely selecting the target/aptamer candidate complex peak as the collection region, the ssDNA library with low binding ability which has dissociated in the meantime could be removed, and thus, an improvement in aptamer yield rate can be expected.

Moreover, in comparison to the conventional CE-SELEX, the present invention has a superior yield rate. Therefore, a desired aptamer could be selected with a fewer number of rounds.

Hereinbelow, the points of difference of the present invention to the conventional SELEX are shown.

TABLE 1

|  | General SELEX | Conventional CE-SELEX | MB-CE-SELEX |
| --- | --- | --- | --- |
| Range of target molecules | Wide | Narrow | Wide |
| Number of rounds | 10~ | 1~4 | ~3 |
| Support | Necessary | Not necessary | Necessary |
| Examination of the selection conditions | — | Difficult | Easy |
| Aptamer yield rate (* Results of the present study) | — | 23% | 91% |

DESCRIPTION OF EMBODIMENTS

Figure 1:
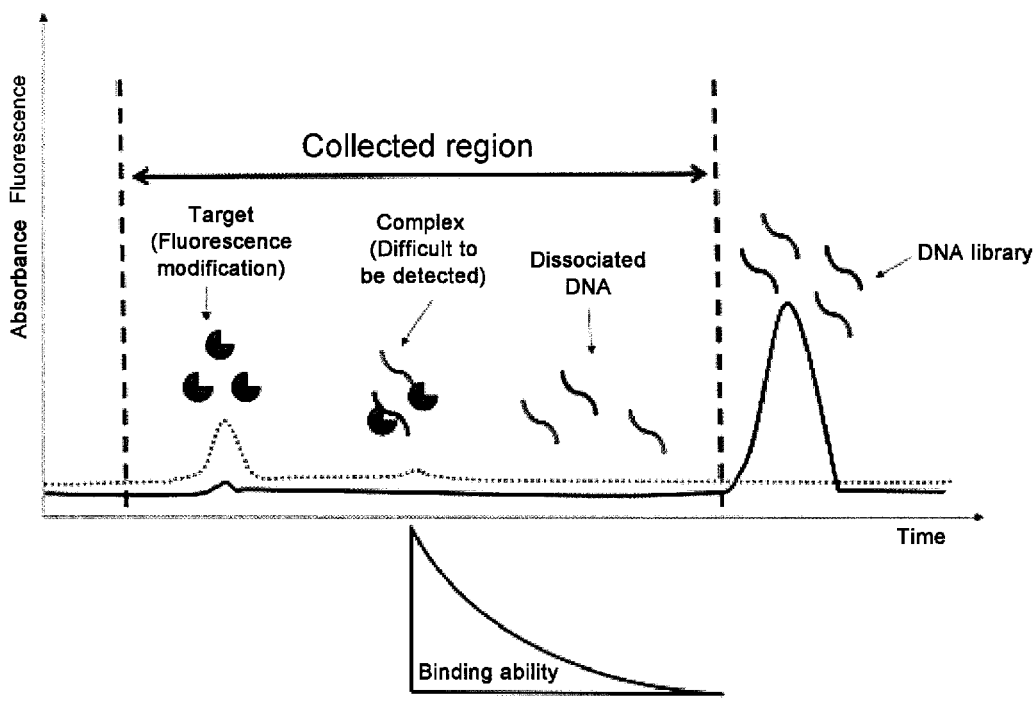
FIG. 1 shows the points of difference of the present invention to the conventional CE-SELEX.
Figure 1:
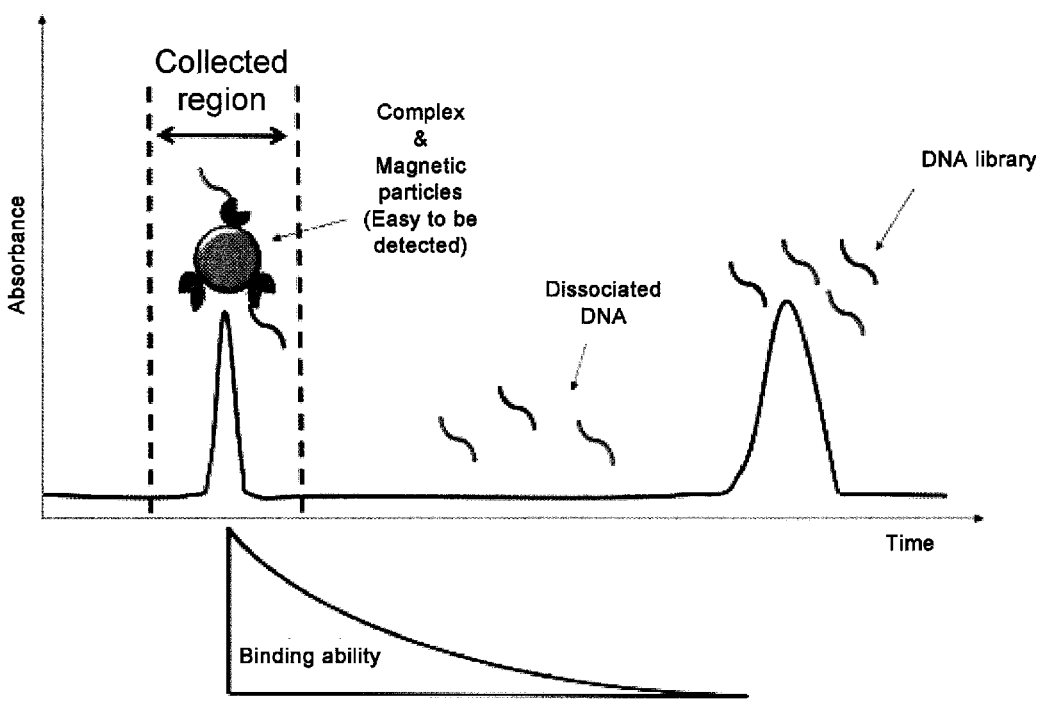

Hereinafter, the present invention is further explained in details in the Examples. Nonetheless, the present invention would not be restricted to these Examples.

Example 1

Immobilization of the Target Molecules to the Magnetic Particles

Magnetic particles having a carboxy group on the surface Dynabeads MyOne (Trade Mark) Carboxylic Acid (Invitrogen) were used as a support and immobilization of the molecules was carried out according to the protocol attached to the product. Hundred μl of 20 mM Tris-HCl, 10 mM NaCl, 1 mM $MgCl_2$ buffer (pH7.4) was added and this was preserved at 4° C. as a 10 mg/ml magnetic particle stock solution.

Optimization of Conditions of CE-SELEX

Conditions of Capillary Electrophoresis

Capillary electrophoresis system (Agilent 7100: Otsuka Electronics Co., Ltd.) was used. As for the capillary, a 75 μm inner diameter bubble cell fused-silica capillary (Agilent technologies) of 80.6 cm in length and of 72.2 cm in effective length (the length up to the detection window) was used. The capillary was set on a cassette so that capillaries of the same length would leave from between the inlet side (injection inlet, positively charged electrode) and the outlet side (elution outlet, negatively charged electrode). As a pre-treatment, by applying a pressure of about 1 bar, a 0.1 M NaOH aqueous solution was allowed to run for 10 to 20 minutes. Furthermore, the capillary was equilibrated by running a running buffer (100 mM borate buffer, pH 8.5) for 10 to 20 minutes.

Separation and Collection of ssDNA Binding to a Target

Preparation of the Samples

Thrombin of the target protein and ssDNA library were dissolved or diluted in a sample buffer (20 mM Tris-HCl, 10 mM NaCl, 1 mM $MgCl_2$ buffer, pH 7.4). For the ssDNA library, a synthetic oligo DNA of a total of 70 mers in which the two ends (5' end and 3' end) of a 30 mer random sequence being sandwiched with a 20 mer immobilized sequence was used. A sample buffer and 100 μm of ssDNA library were placed in a PCR tube which was mixed by pipetting. The ssDNA library solution was heated at 95° C. for 2 minutes by a thermal cycler (TAKARA BIO INC.) and annealing was carried out by cooling down to 25° C. at a rate of 0.1° C./sec.

Sample Injection

After annealing, 2 μM thrombin or 1 μl of 5 to 10 mg/ml thrombin-immobilized magnetic particle solution was added and incubated at room temperature (25° C.) for 30 minutes or more. The target/ssDNA library mixed solution was injected from the inlet side of the capillary by applying a pressure of 100 mbar for 6 to 9 seconds. Based on the Hagen-poiseuille law, an approximate amount of injection could be predicted from the below-mentioned formula. V represents the amount of injection (nl), ΔP represents pressure change (bar), d represents the inner diameter of the capillary (m), π represents the ratio of a circle's circumference to its diameter, T represents injection time (s), η represents solution viscosity, and L represents the total length of the capillary (m).

$$V = \Delta P d^4 \pi T / 128 \eta L \times 10^{12} [nL]$$

Electrophoresis Samples

A vial which contains 50 μl of running buffer was each placed at the inlet side (injection inlet, positively-charged electrode side) and outlet side (elution outlet, negatively-charged electrode side) and a 30 kV constant voltage was applied to carry out electrophoresis. During electrophoresis, absorbance at 195, 260, 280, and 550 nm were measured over time by a diode array detector. The electrophoresis rate was assumed to be always constant and by calculating the elution time from the below-mentioned formula, the collection time was set. T elution represents elution time, T detection represents detection time, L total length represents the total length of the capillary, and L effective length represents the effective length of the capillary.

$$T_{elution} = T_{detection} \times L_{total\ length} / L_{effective\ length}$$

Recovery of Sample

The collected sample using thrombin-immobilized magnetic particles was heated at 95° C. for 10 minutes using a thermal cycler to degenerate the proteins of the magnetic particle surface, and thereby ssDNA was released. This was allowed to stand still for 1 minute on a magnet stand, and the supernatant was recovered.

Amplification of the Collected Sample by PCR

The collected ssDNA sample obtained by capillary electrophoresis was amplified by PCR. In a 1.5 ml tube, 400 µl of 2× premix, 192 µl of DEPC treated water, 80 µl of 4 µM of forward primer, and 80 µl of 4 µM of 5'-biotinylated reverse primer, were placed and mixed. These were aliquoted into eight 200 µl PCR tubes, each tube containing 94 µl of the solution. To each of the 6 tubes, 6 µl of the collected sample was added, and to the remaining 2 tubes, 6 µl of 1-10 µM ssDNA library and 6 µl of DEPC treated water were added as a positive and negative control, respectively. Using a thermal cycler (TAKARA BIO INC.), this was heated at 94° C. for 1 minute, and an operation such as "94° C. for 15 seconds, 55° C. for 5 seconds, and 72° C. for 20 seconds" was repeated for 23 to 28 times. Once PCR was over, whether the target size DNA was amplified was examined by a polyacrylamide gel electrophoresis (PAGE). Once electrophoresis was carried out, the gel was soaked in a staining solution and shaked for 10 minutes. DNA bands after staining were detected by using an UV irradiator.

Purification and Formation of a Single Strand of PCR Products

PCR products were made into a single strand and then made as an ssDNA library to be used in the next round. By using a magnosphere MS300/Streptavidin (Invitrogen) which is a streptavidin-immobilized magnetic particle, the immobilization and washing procedures were carried out according to the attached instruction. Fifty µl of 0.1 M NaOH previously prepared was added, which was subjected for 10 to 15 times of gentle pipetting for suspension and then this was allowed to stand still at room temperature for 4 minutes to release/extract aptamer candidates.

Base Sequence Analysis Using a Next Generation Sequencer

Sample Preparation and Emulsion PCR

Samples for emulsion PCR is prepared according to protocol referred to as Publication Number MAN0007220, Rev.5.0, and by using PAGE, whether the target size DNA was amplified or not was confirmed. After that, column purification of the PCR product was carried out using Fast Gene Gel/PCR Extraction Kit (Nippon Genetics Co., Ltd.). Finally, emulsion PCR and beads purification were carried out using Ion OneTouch™ 2 system (Life Technologies) and Ion PGM Template OT2 200 Kit (Life Technologies).

A Large-Scale Sequence Analysis Using a Next Generation Sequencer

Using a purified beads after emulsion PCR, a large-scale sequence analysis using Ion PGM system (Life technologies), semiconductor chip Ion 314 chip, Ion 318 chip (Life technologies), and Ion PGM Sequencing 200 Kit v2 (Life technologies) was carried out. The operation was carried out according to the attached protocol (Publication Number MAN0007273, Rev.3.0). The sequence data was output to a FASTAQ file, and the sequence of the primer region (immobilized sequence) of the DNA library was removed using CLC Genomics Workbench (CLC bio) and only random sequences of 28 to 32 mers were extracted. Furthermore, the count number of repeated sequence was checked and the sequence information was output to an excel file. The sequence was converted into FASTA format on Excel (microsoft) which was output to a text file. Alignment was made using Mafft and similar sequences (family sequences) were extracted. Furthermore, MEME suite 4.11.0 was used to study the family sequences.

Assessment of the Binding Ability of the Selected Aptamer Immobilization of the Target Protein to a Sensor Chip Using Biacore X100 (GE healthcare), immobilization of the target protein to a sensor surface and the interaction analysis of the target protein with the aptamer were carried out in accordance to the attached manual.

HBS-EP (HEPES, 150 mM NaCl, pH7.0) was used as a running buffer. A carboxymethyl dextran-modified CMS sensor chip (GE healthcare) was set in the flow path, EDC/NHS solution was allowed to flow for 7 minutes at a flow rate of 10 µl/min and the carboxy group on the sensor chip was activated. Ten to twenty µg/ml of thrombin solution diluted with a 10 mM acetic acid/sodium acetate buffer, pH 6.0, was allowed to flow for 7 minutes. Finally, ethanolamine was allowed to flow for 7 minutes to block and complete the coupling reaction.

Calculation of dissociation constant using interaction analysis Aptamer candidate samples were diluted to 2 to 4 µM with a running buffer. After heating for 2 minutes at 95° C. using a thermal cycler, annealing was performed by cooling to 25° C. at a rate of 0.1° C./sec. After annealing, it was further diluted with a running buffer to 50-200 nM. The thrombin-immobilized chip was set in the flow path and this was investigated whether a specific response was demonstrated when the diluted aptamer candidate was allowed to flow at a flow rate of 30 µl/min. As a regeneration solution, 1 M NaCl solution was used. For aptamer candidates demonstrating specific responses, a plural number of dilution samples were adjusted in the range of 6.25-400 nM and multi-kinetic analysis was performed. However, for aptamer candidates that could not be regenerated with a 1 M NaCl solution, single kinetic analysis (which does not have a regeneration process in between) was performed. Evaluation software was used to calculate the dissociation constant.

Identification of Thrombin Aptamer Candidate Sequence by a Next Generation Sequencer The procedures and results for determining the thrombin aptamer candidate sequence using the next generation sequencer are given below.

Large-Scale Sequence Analysis

The aptamer candidate sequences obtained in each round (1st to 3rd round) of the conventional CE-SELEX, MB-CE-SELEX (first round), and MB-CE-SELEX (improved version) were analyzed by a next generation sequencer (Ion PGM system). The total number of read sequences per round was 90000 to 800000 (Table 2). Of the sequences of the 3rd round obtained by each selection method, analysis was proceeded mainly on the 10 sequences with large count numbers. Their sequences were named as follows: T_apt. 1 to 10 (conventional CE-SELEX), T_beads_apt. 1 to 10 (MB-CE-SELEX), T_beads_re_apt. 1 to 10 (MB-CE-SELEX improved version).

Table 2 Total read number of the aptamer candidate sequences selected in each round

TABLE 2

| Selection Method | Read Number | | |
|---|---|---|---|
| | R1 | R2 | R3 |
| Conventional CE-SELEX | 799730 | 804061 | 418048 |
| CE-SELEX introduced with magnetic particles | 96988 | 395167 | 283822 |
| Improved version of CE-SELEX introduced with magnetic particles | 181248 | 165641 | 97890 |

Calculation of the concentration efficiency of the higher ranking base sequences First of all, the presence rate "(the count number of each sequence/the number of total read sequences)×100(%)" of the higher ranking sequence was examined. As a result of this, it was found that the presence rate of the most concentrated sequence in each selection method was as follows: 0.16% for conventional CE-SELEX, 12% for MB-CE-SELEX and 5.1% for MB-CE-SELEX (improved version) (Table 3). According to the paper related to the acquisition of VEGF aptamer using CE-SELEX, which was reported by Bowser et al., an assumption is made that the aptamers acquired by CE-SELEX is rich in diversity and certain sequences are difficult to be concentrated, and in fact, the presence rate of the sequence which was most concentrated at the end of the 4th round was around 0.8%. In comparison to the results of the present study, as for the presence rate of the high ranking sequences obtained by the conventional CE-SELEX, a similar tendency was found as in the prior studies. On the other hand, as for the presence rate of the high ranking sequences obtained by MB-CE-SELEX selection, a high presence rate of approximately 50 to 100 times higher than that obtained by conventional CE-SELEX was demonstrated, and it was revealed that it shows a considerably high concentration effect as compared to that of the prior studies. Moreover, it is believed that a condition that is likely to concentrate an ssDNA having a specific binding ability exists in MB-CE-SELEX.

Table 3 Count number/presence rate of the high ranking sequence per round in the 3$^{rd}$ round of each selection method

TABLE 3

| | Sequences of the random region (5'→3') | Count number | | | Presence rate (%) | | |
|---|---|---|---|---|---|---|---|
| | | R1 | R2 | R3 | R1 | R2 | R3 |
| Conventional CE-SELEX | | | | | | | |
| T_apt.1 | GTTTGGGTGGTTAGGTGTTGACCTGGGATG (SEQ ID NO: 34) | 4 | 143 | 667 | 0.00050 | 0.018 | 0.16 |
| T_apt.2 | GAGTCGGGTGGCTATTGGGTATGGACCGTG (SEQ ID NO: 35) | 5 | 151 | 666 | 0.00063 | 0.019 | 0.16 |
| T_apt.3 | GATGGTGTAGGTTGGGAGAGGCTCAGTGCC (SEQ ID NO: 36) | 4 | 64 | 266 | 0.00050 | 0.0080 | 0.064 |
| T_apt.4 | TTGGTGGGGTGGCTTTGGGTATTTACTTGG (SEQ ID NO: 37) | 3 | 30 | 195 | 0.00038 | 0.0037 | 0.047 |
| T_apt.5 | GTGGATTTGGGTGGATTGGTATGAACTGAC (SEQ ID NO: 38) | 5 | 40 | 181 | 0.00063 | 0.0050 | 0.043 |
| T_apt.6 | GTTGGGTAGGGTTGGATAGGGGCAAGTAGA (SEQ ID NO: 39) | 0 | 45 | 180 | 0 | 0.0056 | 0.043 |
| T_apt.7 | GTGTACTATTATGGTGTGGTTGGTATGGTT (SEQ ID NO: 40) | 2 | 64 | 174 | 0.00025 | 0.0080 | 0.042 |
| T_apt.8 | GGTTGGGTGGTGTGGGTAGTGATCCCTGTG (SEQ ID NO: 41) | 1 | 39 | 154 | 0.0013 | 0.0049 | 0.037 |
| T_apt.9 | TGGATTGGTTGGATTGGGGGTGTGACTGTG (SEQ ID NO: 42) | 0 | 26 | 138 | 0 | 0.0032 | 0.033 |
| T_apt.10 | TCGGGTTGGATTGGTTGGCTTAAACTATGT (SEQ ID NO: 43) | 3 | 58 | 93 | 0.00038 | 0.0072 | 0.022 |
| TBA_like_apt.1 | TCTGGTTGGTGTGGTTGGGAGTTTTTTGATC (SEQ ID NO: 44) | 1 | 4 | 6 | 0.000125042 | 0.00050 | 0.0014 |
| CE-SELEX introduce with magnetic particles | | | | | | | |
| T_beads_apt.1 | GATGGTGTAGGTTGGGAGAGGCTCAGTGCC (SEQ ID NO: 45) | 2 | 8110 | 34268 | 0.0021 | 2.1 | 12 |
| T_beads_apt.2 | GTTTGGGTGGTTAGGTGTTGACCTGGGATG (SEQ ID NO: 46) | 0 | 2251 | 4673 | 0 | 0.57 | 1.65 |
| T_beads_apt.3 | GATGGTGTAGGTTGGGAGAGGCTCAGTGC (SEQ ID NO: 47) | 0 | 225 | 1059 | 0 | 0.057 | 0.37 |
| T_beads_apt.4 | TTAGGGTTGGGAGGGTGGCTGACTAATGTA (SEQ ID NO: 48) | 0 | 5 | 1035 | 0 | 0.0013 | 0.36 |

TABLE 3-continued

| | Sequences of the random region (5'→3') | Count number | | | Presence rate (%) | | |
|---|---|---|---|---|---|---|---|
| | | R1 | R2 | R3 | R1 | R2 | R3 |
| T_beads_apt.5 | GAGTCGGGTGGCTATTGGGTATGGACCGTG (SEQ ID NO: 49) | 0 | 5 | 853 | 0 | 0.0013 | 0.31 |
| T_beads_apt.6 | GGGTTGGATTGGGTGGCGGTGTGAACTATG (SEQ ID NO: 50) | 0 | 0 | 800 | 0 | 0 | 0.28 |
| T_beads_apt.7 | GTTGGTTATGGTGGTTTTAGTGGGACTCGA (SEQ ID NO: 51) | 0 | 5 | 532 | 0 | 0.0013 | 0.19 |
| T_beads_apt.8 | ATAGGATGGGTGGGTGGGTTCGTCAGTTA (SEQ ID NO: 52) | 0 | 3 | 270 | 0 | 0.0008 | 0.10 |
| T_beads_apt.9 | TGGGTCCGGGGTTGGGGGGGTGGCCGGGTC (SEQ ID NO: 53) | 0 | 0 | 260 | 0 | 0 | 0.092 |
| T_beads_apt.10 | GGGTGGGGTGGATTGGTTGGCGTTCCTGGA (SEQ ID NO: 54) | 0 | 2 | 246 | 0 | 0.00051 | 0.087 |
| CE-SELEX introduced with magnetic particles (Improved version) | | | | | | | |
| T_beads_re_apt.1 | AAGAGGGTGGAGTGGTTGGCTTCACAATGG (SEQ ID NO: 55) | 0 | 17 | 4979 | 0 | 0.010 | 5.1 |
| T_beads_re_apt.2 | GTTGGTTATGGTGGTTTTAGTGGGACTCGA (SEQ ID NO: 56) | 0 | 17 | 2244 | 0 | 0.010 | 2.3 |
| T_beads_re_apt.3 | GGGGTGGATGTGGTATTTTAGTGGCGATCT (SEQ ID NO: 57) | 0 | 5 | 940 | 0 | 0.0030 | 0.96 |
| T_beads_re_apt.4 | AAGGGGTGGGGGTCGGGTGGCCTCACGAT (SEQ ID NO: 58) | 0 | 7 | 844 | 0 | 0.0042 | 0.86 |
| T_beads_re_apt.5 | GGATGGATTGGTTGGCGTCTGATAATGGTG (SEQ ID NO: 59) | 0 | 7 | 643 | 0 | 0.0042 | 0.66 |
| T_beads_re_apt.6 | GTTTGGGTGGTTAGGTGTTGACCTGGGATG (SEQ ID NO: 60) | 2 | 191 | 549 | 0.0011 | 0.12 | 0.56 |
| T_beads_re_apt.7 | GATGGTGTAGGTTGGGAGAGGCTCAGTGCC (SEQ ID NO: 61) | 1 | 105 | 540 | 0.00055 | 0.053 | 0.55 |
| T_beads_re_apt.8 | TTGGTGGGGTGGCTTTGGGTATTTACTTGG (SEQ ID NO: 62) | 2 | 55 | 475 | 0.0011 | 0.033 | 0.49 |
| T_beads_re_apt.9 | GGGGATGGTTAGGGTGGCTTAATATTGACC (SEQ ID NO: 63) | 0 | 8 | 450 | 0 | 0.005 | 0.46 |
| T_beads_re_apt.10 | ACGGGGATGGGGGGGTGGAGGAGGCCTGT (SEQ ID NO: 64) | 0 | 6 | 438 | 0 | 0.004 | 0.45 |

Binding Ability of Aptamer Candidate Sequence

Table 4 shows the binding ability of each candidate sequence to thrombin calculated by using a surface plasmon resonance (SPR) sensor.

Figure 2:
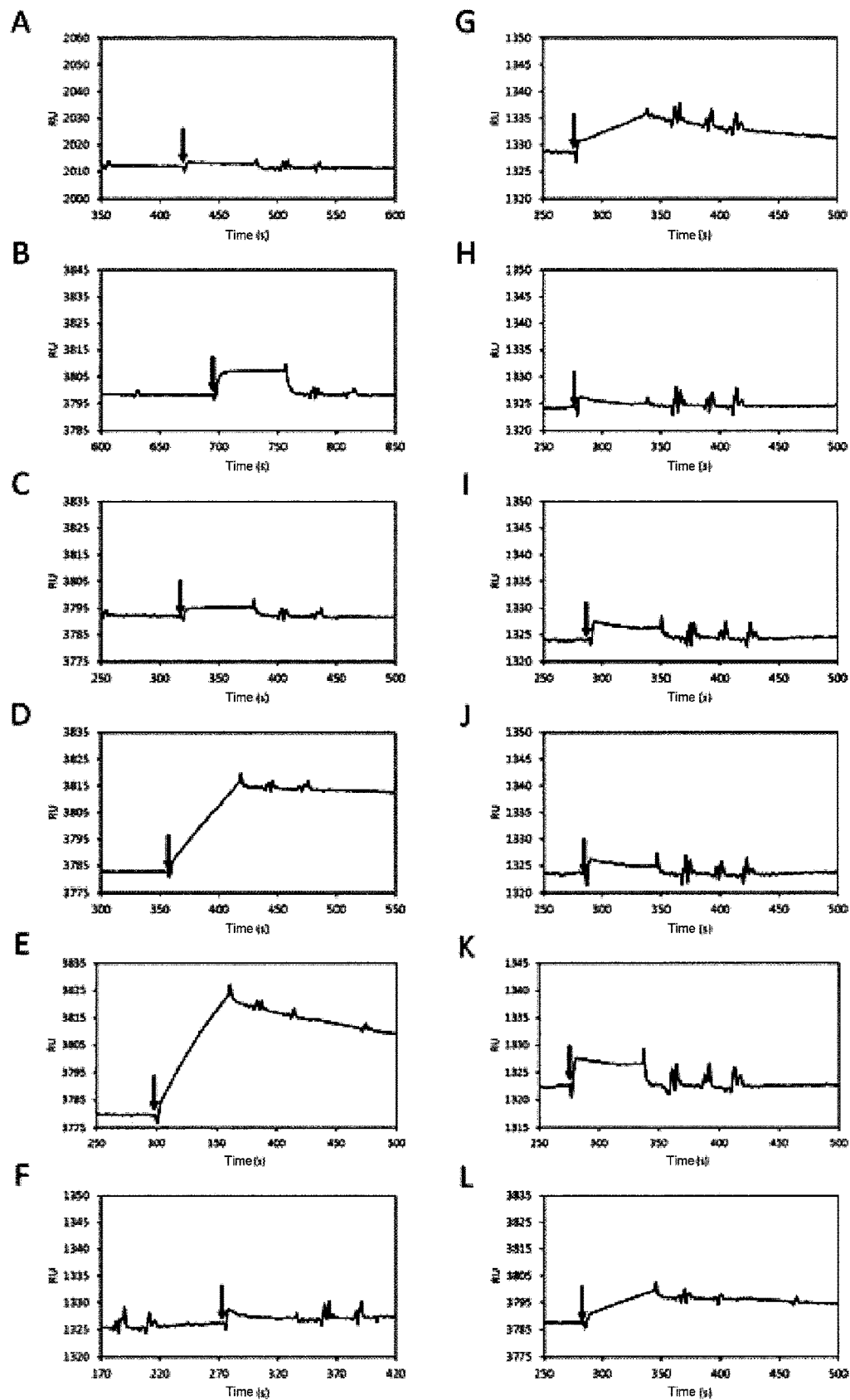
FIG. 2 shows assessment of the binding ability of thrombin aptamer candidates by an SPR sensor (conventional CE-SELEX). Each figure A to J (in total 10) shows the results of examining 10 aptamer candidate sequences shown in the upper row of Table 3.

Comparing the Aptamer Yield Rates Between the Conventional CE-SELEX and MB-CE-SELEX Of the high ranking sequences, by comparing the ratio of sequences having a high binding ability to thrombin, the performance of the novel MB-CE-SELEX was assessed. First, the presence of the binding ability of the higher ranking sequence (in total 10 sequences) obtained by conventional CE-SELEX was examined (FIG. 2). The preliminary experiments revealed that thrombin did not interact non-specifically with ssDNA, as no increase in specific response was observed in the ssDNA library (FIG. 2A). Of T_apt. 1 to 10, in 3 aptamer candidates such as T_apt. 3, T_apt. 4, and T_apt. 6, specific response was obtained (FIGS. 2B to 2K). With respect to, T_apt. 1 and T_apt. 10, although a slight increase in response was observed, the binding ability was considered to be low because the shape of the peak was of a box shape, i.e., dissociation was very fast (FIG. 2B, K). As a control, a binding experiment was carried out for TBA_like_apt. 1 having the exact same sequence as TBA 15, and a specific response was obtained (FIG. 2L).

Figure 3:
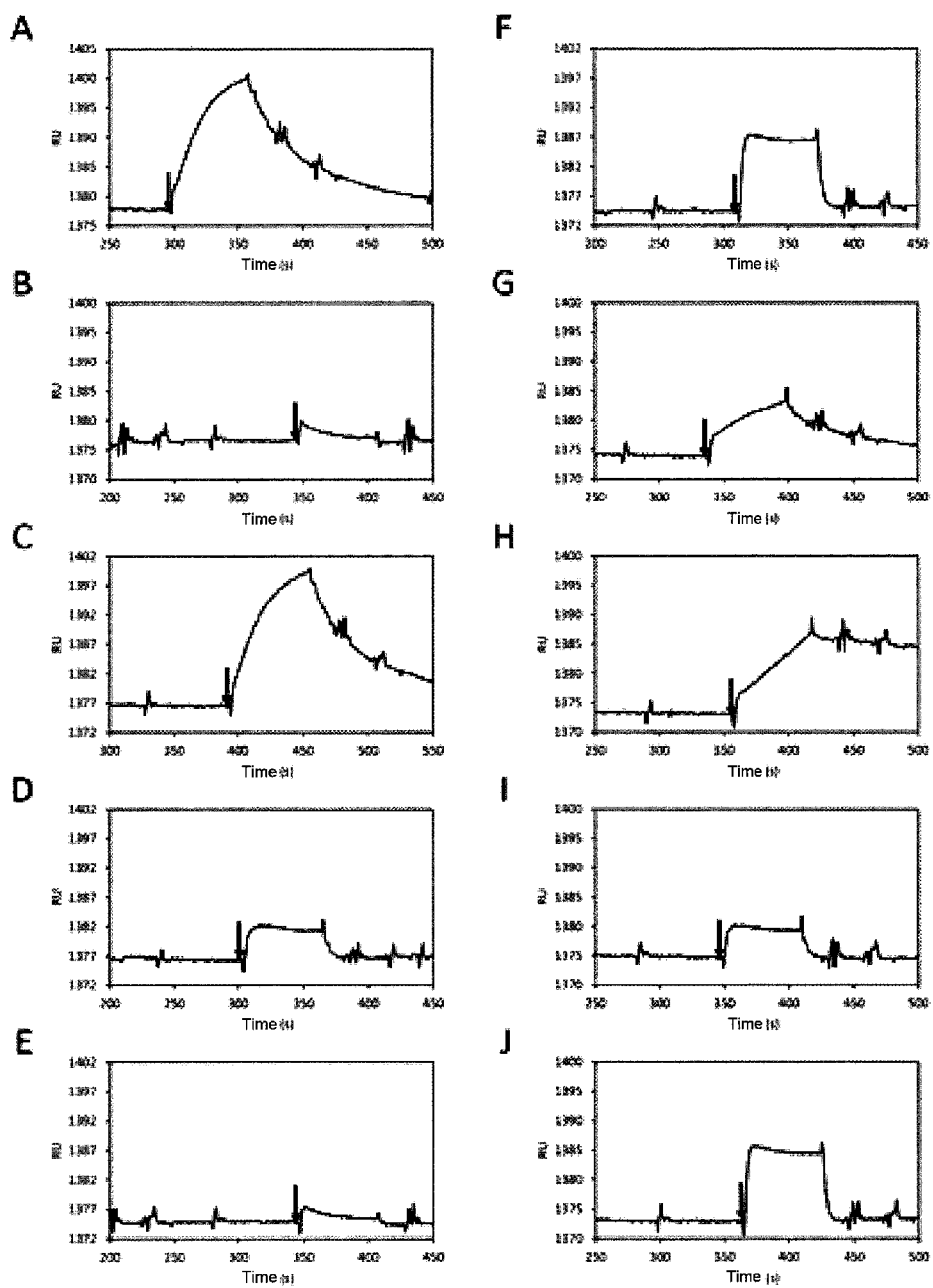
FIG. 3 shows assessment of the binding ability of thrombin aptamer candidates by an SPR sensor (MB-CE-SELEX of the present invention). Each figure A to J (in total 10) shows the results of examining 10 aptamer candidate sequences shown in the middle row of Table 3.

Similarly, as a result of studying the presence of the binding ability in the higher ranking sequences (in total 10 sequences) obtained by MB-CE-SELEX, in 4 aptamer candidates such as T_beads_apt. 1, T_beads_apt. 3, T_beads_apt. 7, and T_beads_apt. 8, a specific response was obtained (FIG. 3).

Figure 4:
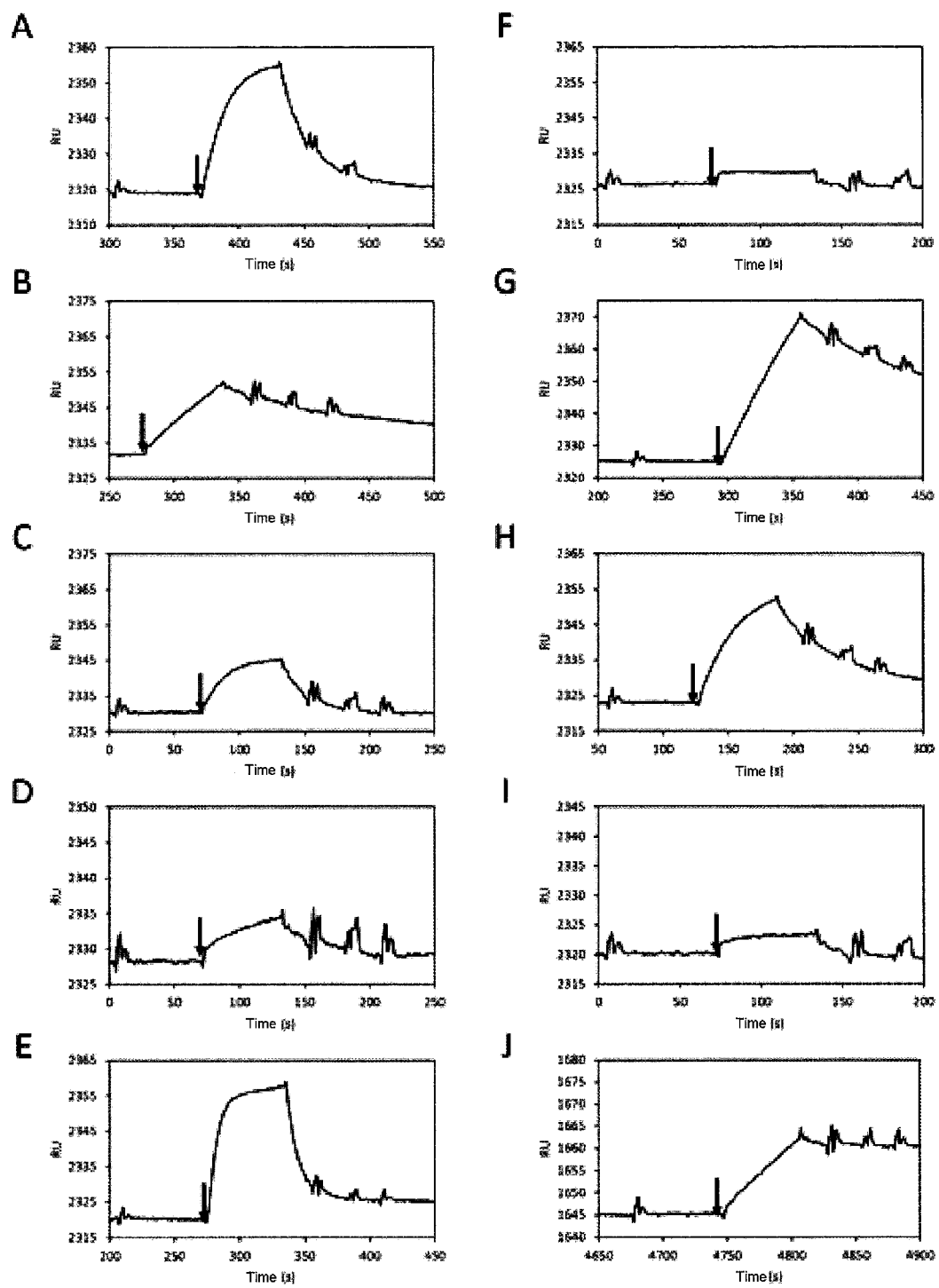
FIG. 4 shows assessment of the binding ability of thrombin aptamer candidates by an SPR sensor (MB-CE-SELEX of the present invention, improved version). Each figure A to J (in total 10) shows the results of examining 10 aptamer candidate sequences shown in the bottom row of Table 3.
Figure 5:
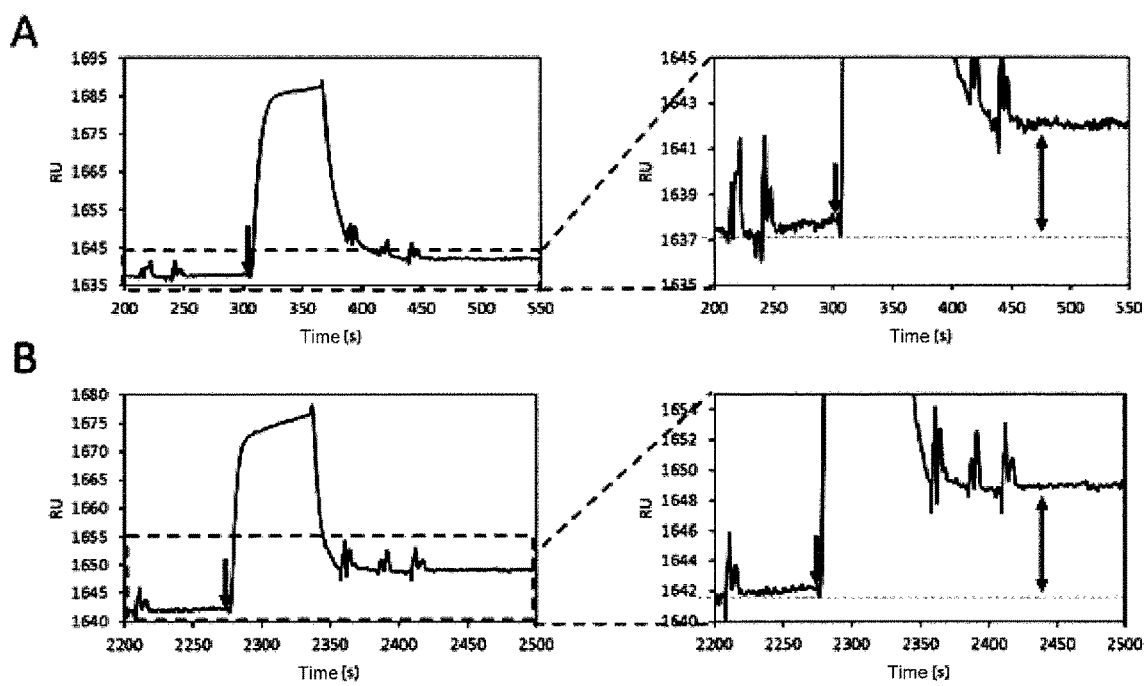
FIG. 5 shows a unique dissociation phase of T_beads_re_apt.1 and T_beads_re_apt.5. (A) The response curve of 200 nM T_beads_re_apt.1 and the enlarged image. (B) The response curve of 200 nM T_beads_re_apt.5 and the enlarged image.

Finally, as a result of studying the presence of the binding ability in the higher ranking sequences (in total 10 sequences) obtained by MB-CE-SELEX (improved version), in 8 aptamer candidates other than T_beads_re_apt. 6, and T_beads_apt. 9, a specific response was obtained (FIG. 4). In particular, with respect to T_beads_re_apt. 1 and T_beads_re_apt. 5, a unique response curve that cannot be found in other aptamers was obtained. These two aptamers, after drawing a relatively fast dissociation curve, maintained a certain level of response (FIG. 5). In other words, it was considered that a condition exists that a certain number of aptamers were firmly bound to thrombin and did not separate.

Figure 6:
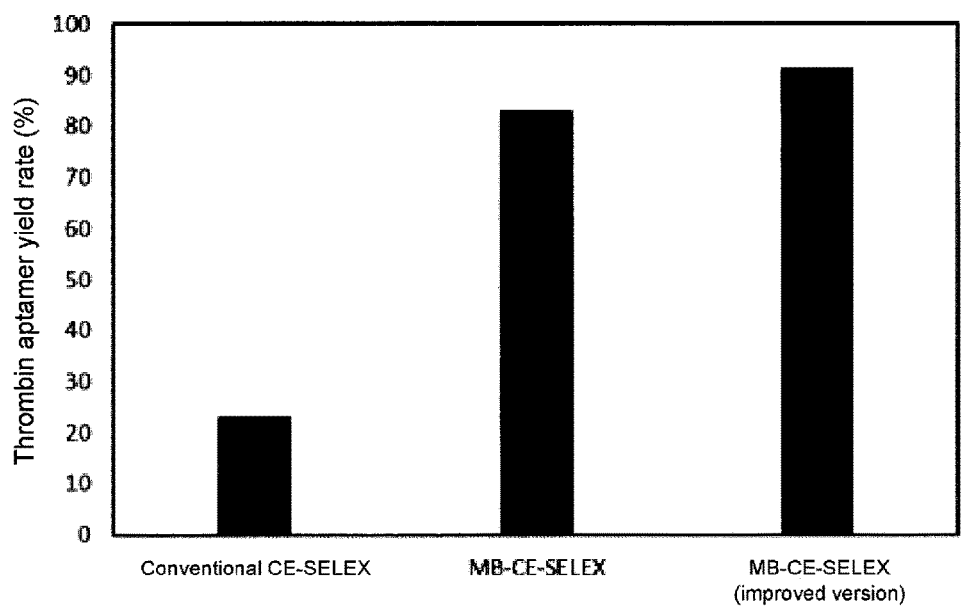
FIG. 6 shows the yield rate of thrombin aptamers in each selection method (calculated based only on the top 10 sequences). Conventional CE-SELEX: 23%; MB-CE-SELEX: 83%; MB-CE-SELEX (improved version): 91%

Of the higher ranking sequence of each selection method, the ratio of those showing high binding ability was as follows: 3/10 for conventional CE-SELEX, 4/10 for MB-CE-SELEX, and 8/10 for MB-CE-SELEX (improved version). The aptamer yield rate (the sum of the count numbers of the sequences having high binding ability/the sum of the count numbers of the sequences whose binding ability was examined) from the count number (the presence rate) of the 10 sequences of each set of high ranking sequences was calculated as follows: 23% in the conventional CE-SELEX, 83% in MB-CE-SELEX and 91% in MB-CE-SELEX (improved version) (FIG. 6). In MB-CE-SELEX, it was revealed that thrombin aptamers could be acquired with a higher probability than the conventional CE-SELEX.

Calculation of dissociation constant of thrombin aptamer With respect to a sequence from which a specific response curve was obtained, the binding rate constant (ka), the dissociation rate constant (kd), and the dissociation constant KD were calculated by multi-kinetic analysis or single kinetic analysis (FIG. 7, Table 4). With respect to T_beads_re_apt. 10, dissociation constant was calculated by single kinetic analysis (FIG. 7J) since dissociation was very slow and even with high concentrations of NaCl, they did not dissociate from thrombin. T_beads_re_apt. 1 and T_beads_re_apt. 5 are likely to have a high binding ability, but it is difficult to calculate the dissociation rate (kd) because no slope is present in the dissociation curve (Figures A and E), and the dissociation constant (KD) was unable to be calculated by an SPR sensor.

The binding rate constant, the dissociation rate constant, and the dissociation constant in the high ranking sequences in the 3rd round of each selection method

TABLE 4

| | Sequences of the random region (5'→3') | $ka(M^{-1}s^{-1})$ | SE(ka) | $kd(s^{-1})$ | SE(kd) | KD(nM) |
|---|---|---|---|---|---|---|
| Conventional CE-SELEX | | | | | | |
| T_apt.1 | GTTTGGGTGGTTAGGTGTTGACCTGGGATG (SEQ ID NO: 34) | — | — | — | — | — |
| T_apt.2 | GAGTCGGGTGGCTATTGGGTATGGACCGTG (SEQ ID NO: 35) | — | — | — | — | — |
| T_apt.3 | GATGGTGTAGGTTGGGAGAGGCTCAGTGCC (SEQ ID NO: 36) | $1.8 \times 10^5$ | $4.4 \times 10^3$ | $1.4 \times 10^{-2}$ | $1.3 \times 10^{-4}$ | 76 |
| T_apt.4 | TTGGTGGGGTGGCTTTGGGTATTTACTTGG (SEQ ID NO: 37) | $1.1 \times 10^5$ | $1.7 \times 10^3$ | $9.0 \times 10^{-3}$ | $5.3 \times 10^{-5}$ | 81 |
| T_apt.5 | GTGGATTTGGGTGGATTGGTATGAACTGAC (SEQ ID NO: 38) | — | — | — | — | — |
| T_apt.6 | GTTGGGTAGGGTTGGATAGGGGCAAGTAGA (SEQ ID NO: 39) | $7.1 \times 10^4$ | $2.7 \times 10^3$ | $4.0 \times 10^{-3}$ | $1.1 \times 10^{-4}$ | 55 |
| T_apt.7 | GTGTACTATTATGGTGTGGTTGGTATGGTT (SEQ ID NO: 40) | — | — | — | — | — |
| T_apt.8 | GGTTGGGTGGTGTGGGTAGTGATCCCTGTG (SEQ ID NO: 41) | — | — | — | — | — |
| T_apt.9 | TGGATTGGTTGGATTGGGGGTGTGACTGTG (SEQ ID NO: 42) | — | — | — | — | — |
| T_apt.10 | TCGGGTTGGATTGGTTGGCTTAAACTATGT (SEQ ID NO: 43) | — | — | — | — | — |
| TBA_like_apt.1 | TCTGGTTGGTGTGGTTGGGAGTTTTTTGATC (SEQ ID NO: 44) | $3.8 \times 10^4$ | $1.3 \times 10^3$ | $8.3 \times 10^{-3}$ | $1.3 \times 10^{-4}$ | 217 |
| CE-SELEX introduce with magnetic particles | | | | | | |
| T_beads_apt.1 | GATGGTGTAGGTTGGGAGAGGCTCAGTGCC (SEQ ID NO: 45) | $1.8 \times 10^5$ | $4.4 \times 10^3$ | $1.4 \times 10^{-2}$ | $1.3 \times 10^{-4}$ | 76 |
| T_beads_apt.2 | GTTTGGGTGGTTAGGTGTTGACCTGGGATG (SEQ ID NO: 46) | — | — | — | — | — |
| T_beads_apt.3 | GATGGTGTAGGTTGGGAGAGGCTCAGTGC (SEQ ID NO: 47) | $1.4 \times 10^5$ | $7.2 \times 10^3$ | $2.2 \times 10^{-2}$ | $9.9 \times 10^{-4}$ | 165 |
| T_beads_apt.4 | TTAGGGTTGGGAGGGTGGCTGACTAATGTA (SEQ ID NO: 48) | — | — | — | — | — |
| T_beads_apt.5 | GAGTCGGGTGGCTATTGGGTATGGACCGTG (SEQ ID NO: 49) | — | — | — | — | — |

TABLE 4-continued

| | Sequences of the random region (5'→3') | ka(M$^{-1}$s$^{-1}$) | SE(ka) | kd(s$^{-1}$) | SE(kd) | KD(nM) |
|---|---|---|---|---|---|---|
| T_beads_apt.6 | GGGTTGGATTGGGTGGCGGTGTGAACTATG (SEQ ID NO: 50) | — | — | — | — | — |
| T_beads_apt.7 | GTTGGTTATGGTGGTTTTAGTGGGACTCGA (SEQ ID NO: 51) | 5.1 × 10$^4$ | 2.1 × 10$^3$ | 1.7 × 10$^{-2}$ | 2.6 × 10$^{-4}$ | 329 |
| T_beads_apt.8 | ATAGGATGGGTGGGTGGGTTCGTCAGTTA (SEQ ID NO: 52) | 4.7 × 10$^4$ | 6.0 × 10$^2$ | 2.0 × 10$^{-3}$ | 1.7 × 10$^{-5}$ | 43 |
| T_beads_apt.9 | TGGGTCCGGGGTTGGGGGGGTGGCCGGGTC (SEQ ID NO: 53) | — | — | — | — | — |
| T_beads_apt.10 | GGGTGGGGTGGATTGGTTGGCGTTCCTGGA (SEQ ID NO: 54) | — | — | — | — | — |
| CE-SELEX introduced with magnetic particles (Improved version) | | | | | | |
| T_beads_re_apt.1 | AAGAGGGTGGAGTGGTTGGCTTCACAATGG (SEQ ID NO: 55) | * | * | * | * | * |
| T_beads_re_apt.2 | GTTGGTTATGGTGGTTTTAGTGGGACTCGA (SEQ ID NO: 56) | 5.1 × 10$^4$ | 2.1 × 10$^3$ | 1.7 × 10$^{-2}$ | 2.5 × 10$^{-4}$ | 329 |
| T_beads_re_apt.3 | GGGGTGGATGTGGTATTTTAGTGGCGATCT (SEQ ID NO: 57) | 4.6 × 10$^4$ | 1.3 × 10$^4$ | 4.4 × 10$^{-2}$ | 4.0 × 10$^{-3}$ | 947 |
| T_beads_re_apt.4 | AAGGGGGTGGGGGTCGGGTGGCCTCACGAT (SEQ ID NO: 58) | 2.0 × 10$^4$ | 1.2 × 10$^3$ | 1.3 × 10$^{-2}$ | 1.5 × 10$^{-2}$ | 645 |
| T_beads_re_apt.5 | GGATGGATTGGTTGGCGTCTGATAATGGTG (SEQ ID NO: 59) | * | * | * | * | * |
| T_beads_re_apt.6 | GTTTGGGTGGTTAGGTGTTGACCTGGGATG (SEQ ID NO: 60) | — | — | — | — | — |
| T_beads_re_apt.7 | GATGGTGTAGGTTGGGAGAGGCTCAGTGCC (SEQ ID NO: 61) | 1.8 × 10$^5$ | 4.4 × 10$^2$ | 1.4 × 10$^{-2}$ | 1.3 × 10$^{-4}$ | 76 |
| T_beads_re_apt.8 | TTGGTGGGGTGGCTTTGGGTATTTACTTGG (SEQ ID NO: 62) | 1.1 × 10$^5$ | 1.7 × 10$^3$ | 9.0 × 10$^{-3}$ | 5.3 × 10$^{-5}$ | 81 |
| T_beads_re_apt.9 | GGGGATGGTTAGGGTGGCTTAATATTGACC (SEQ ID NO: 63) | — | — | — | — | — |
| T_beads_re_apt.10 | ACGGGGATGGGGGGGTGGAGGAGGCCTGT (SEQ ID NO: 64) | 6.0 × 10$^3$ | 6.8 × 10 | 6.0 × 10$^{-4}$ | 6.0 × 10$^{-5}$ | 101 |

In MB-CE-SELEX (improved version), as the aptamer yield rate (the sum of the count numbers of sequences having high binding ability/the sum of the count numbers of the sequences examining the binding ability) increases, nucleic acid aptamers with smaller dissociation rate constant (difficult to dissociate) were mainly obtained. For example, T_beads_re_apt.1 and T_beads_re_apt. 5 having a binding ability binding to a degree so that a slope of the dissociation curve cannot be obtained as well as T_beads_re_apt.10 whose dissociation constant was able to be calculated only by single kinetic analysis, were obtained. The difference of only 18 seconds of the collection region between the first MB-CE-SELEX whose collection window (time) was deliberately expanded and MB-CE-SELEX (improved version) whose collection window (time) was narrowed was revealed to attribute to the aptamer yield rate and the dissociation rate constant. It is possible that the present system may be further improved by optimizing the collection window (time) and by adjusting the peak deriving from the magnetic particles to be sharper.

INDUSTRIAL APPLICABILITY

The present invention is useful for screening nucleic acid aptamers.

The invention claimed is:

1. A method for screening a nucleic acid aptamer comprising:
   (a) contacting a target molecule immobilized on a solid phase support with a nucleic acid aptamer candidate;
   (b) collecting the nucleic acid aptamer candidate binding with the target molecule by a capillary electrophoresis;
   (c) amplifying the nucleic acid aptamer candidate by PCR.

2. The method according to claim 1 further comprising (d) making the amplified PCR product into a single strand.

3. The method according to claim 1, wherein the solid phase support is a particle.

4. The method according to claim 3, wherein the minimum value of the particle size of the particle is 0.05 μm.

5. The method according to claim 1, wherein the target molecule is a protein or a low molecular weight compound.

6. The method according to claim 1, wherein the nucleic acid aptamer candidate is a single-stranded DNA library.

7. The method according to claim 2, wherein the steps (a) to (d) are repeated for a maximum of three times.

* * * * *